(12) United States Patent
Völcker et al.

(10) Patent No.: US 6,686,582 B1
(45) Date of Patent: Feb. 3, 2004

(54) OPTICAL ARRAY SYSTEM AND READER FOR MICROTITER PLATES

(75) Inventors: Martin Völcker, Königsbronn (DE); Jürgen Liegel, Oberkochen (DE); Martin Gulch, Jena (DE)

(73) Assignee: Carl-Zeiss-Stiftung, Heidenbeim (DE)

( * ) Notice: Subject to any disclaimer, the term of this patent is extended or adjusted under 35 U.S.C. 154(b) by 0 days.

(21) Appl. No.: 09/530,612
(22) PCT Filed: Oct. 12, 1998
(86) PCT No.: PCT/EP98/06468
§ 371 (c)(1),
(2), (4) Date: Aug. 7, 2000
(87) PCT Pub. No.: WO99/23474
PCT Pub. Date: May 14, 1999

(30) Foreign Application Priority Data

Oct. 31, 1997 (DE) .......................................... 197 48 211

(51) Int. Cl.[7] .................................................. H01J 3/14
(52) U.S. Cl. ..................................... 250/216; 250/461.2
(58) Field of Search ............................... 250/216, 458.1, 250/461.2, 559.4, 559.44; 356/440; 359/619, 621, 622, 626

(56) References Cited

U.S. PATENT DOCUMENTS

| | | | |
|---|---|---|---|
| 4,362,365 A | * 12/1982 | Esswein | 350/414 |
| 4,710,031 A | * 12/1987 | Kelly et al. | 356/440 |
| 6,177,277 B1 | * 1/2001 | Soini | 436/63 |

FOREIGN PATENT DOCUMENTS

| | | | |
|---|---|---|---|
| DE | 019624421 A1 | * | 1/1997 |
| DE | 019651667 A1 | * | 9/1997 |
| EP | 000679864 A1 | * | 11/1995 |
| WO | WO95/01599 | * | 1/1995 |
| WO | WO97/34171 | * | 9/1997 |

* cited by examiner

Primary Examiner—Que T. Le
Assistant Examiner—Eric Spears

(57) ABSTRACT

An optical system made up of lens arrays and normal lenses is particularly suitable for use as a massive parallel reader (approximately $10^2$ channels) for microtiter plates and the like in absorption, fluorescence and luminescence.

19 Claims, 2 Drawing Sheets

OPTICAL ARRAY SYSTEM AND READER FOR MICROTITER PLATES

CROSS-REFERENCES TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention relates to a reader for microtiter plates or substance chips.

Fluorescence, luminescence, and absorption investigations of huge numbers of very small amounts of samples are necessary in the development of pharmaceutically effective materials, and also in medical molecular diagnosis. Here a high throughput of samples in the measurement is of the greatest importance.

Kinetic measurements are particularly in demand, with time constants which permit a high throughput.

For the preparation of the samples, microtiter plates are available, with small sample holders arranged in a grid pattern in standard configurations with, e.g., 96 or a multiple thereof, e.g., 384 or 1536, sample containers (multi-well microplates). Alternatively, so-called substance chips are also used as sample carriers.

Such a reader is, for example, offered for sale by Molecular Devices Corp., USA, under the designation SPECTRAmax (R) PLUS. A light source and a monochromator are connected by means of 8 optical fibers to 8 mirror optics, each for the transmission illumination of a respective sample holder, and with 8 measuring photodetectors. Eight-fold measurement in parallel is thus possible.

SUMMARY OF THE INVENTION

The invention has as its object to provide a reader for microtiter plates or substance chips which makes possible a massively parallel measurement, and thus to very greatly increases the sample throughput, even for kinematic measurements. High efficiency of the light paths, and a compact construction, as simple as possible, are to be attained thereby. A high measurement sensitivity is of course to be insured.

An optical system attains this object. A reader for microtiterplates or substance chips having a plurality of individual sample volumes arranged in a grid pattern dimension, comprising a lens array having a grid pattern dimension that corresponds to the grid pattern dimension of the individual sample volumes of the microtiterplate or substance chip, a detector array, a reflected light illumination device providing illumination light, a telescope between the lens array and the detector array that effects a reduction to match a beam diameter defined by the lens array to the dimensions of the detector array, and a field lens, wherein a reduced image of the microtiterplate or substance chip is formed on the detector array by a system of the lens array, the telescope, and the field lens, so that on the detector array a strict channel separation results between measurement signals arising from the individual sample volumes of the microtiterplate or substance chip, wherein the lens array is achromatized in that each individual lens of the lens array comprises a lens group with achromatic properties, and wherein the illumination light is conducted through the lens array precisely to locations on the microtiterplate or substance chip which are imaged on the detector array attains the object of the invention. The object of the invention is also attained by a reader for microtiterplates or substance chips having a plurality of individual sample volumes arranged in a grid pattern dimension, comprising: a lens array having a grid pattern dimension that corresponds to the grid pattern dimension of the individual sample volumes of the microtiterplate or substance chip, a detector array, a reflected light illumination device providing illumination light, a telescope between the lens array and the detector array that effects a reduction to match a beam diameter defined by the lens array to the dimensions of the detector array, and a field lens, wherein a reduced image of the microtiterplate or substance chip is formed on the detector array by a system of the lens array, the telescope, and the field lens, so that on the detector array a strict channel separation results between measurement signals arising from the individual sample volumes of the microtiterplate or substance chip, the reader comprising a modular construction with the lens array being interchangeable, and wherein several lens arrays are provided, and wherein the individual lenses of different ones of the several lens arrays provide different numerical apertures also attains the object of the invention. For detection, a detector array is provided which is available, for example, as a CCD array. Conventional optics with conventional lenses are combined with lens arrays over the whole cross section. Imaging of the whole sensed object region (microtiter plate) to the correct scale on the CCD array, and also a suitable imaging of the individual wells of the microtiter plate on the CCD array (two different scales), with strict channel separation between the different wells, are thus both attained.

Advantageously, the features stated in the dependent claims are supplementary to this. These include a telescope, which is single-lens over the cross section; a microlens array before the detector array, and the integration of a reflected light illumination. The latter, by double use of the optical elements, results in particularly good efficiency and particularly good noise suppression, in that exactly the sample volume is illuminated which is also sensed by the detection beam path.

A further suppression of interference can be attained with an aperture array.

BRIEF DESCRIPTION OF THE DRAWINGS

The invention is described in more detail with reference to the drawings.

DETAILED DESCRIPTION OF THE INVENTION

Figure 1:
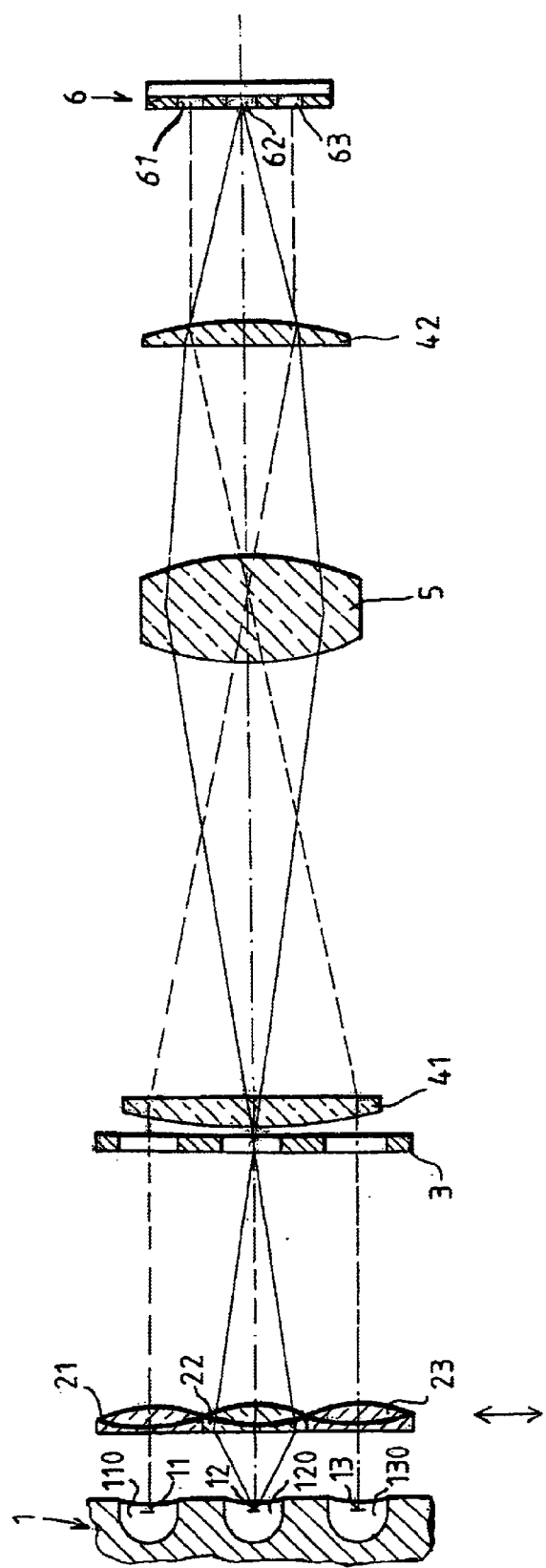
FIG. 1 shows schematically a first optical arrangement according to the invention, in a first embodiment.

The illustration of FIG. 1 shows only three respective examples of all the array elements, in order to be able to illustrate the principle clearly. A practical embodiment provides a match to a conventional microtiter plate array of 8×12=96 elements (pixels).

An object array 11, 12, 13 is formed by the microtiter plate with recesses (wells) and substance samples 110, 120, 130 placed therein. The minilens array 21, 22, 23 has the same grid measurements, and is built up from conventional small lenses, with a focal length of f=7.8 and a numerical aperture of about 0.6, effectively collecting together the light from a central region 11, 12, 13 of the samples 110, 120, 130. An aperture 3 is arranged in the intermediate image plane at a distance of 380 mm, and prevents crosstalk between the individual array elements.

The telescope which follows, having lenses 41 and 42, reduces the beam diameter from 130 mm to 15 mm, matching the dimensions of the CCD array. The field lens 5 arranged therebetween provides imaging of the intermediate image and thus of the array of objects 11, 12, 13 onto the elements of the CCD array 6.

The whole "collective" optics 41, 5, 42 is determined as regards its diameter only by the size of the microtiter plate 1 or of the array of objects 11, 12, 13. In contrast to this, a conventional CCD camera with the same numerical aperture of 0.6 has to have much larger lenses. This is made possible in that the numerical aperture of the optical system according to the invention is determined by the elements 21, 22, 23 of the minilens array.

The most important feature of the arrangement is that a respective image zone on the CCD array corresponds exactly, and free from crosstalk, to each of the samples 110, 120, 130.

Figure 2:
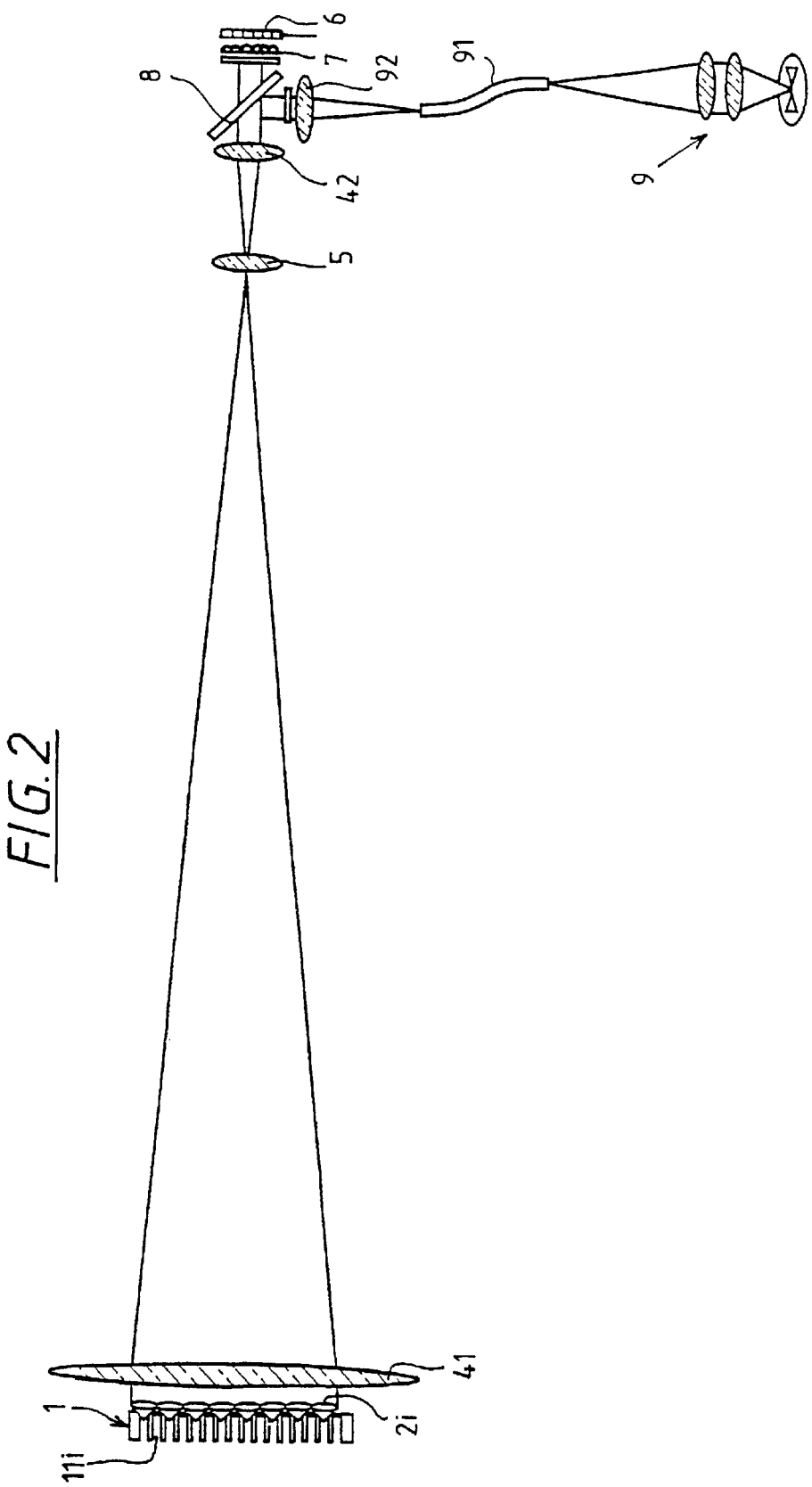
FIG. 2 shows schematically a reader according to the invention.

The illumination device would have to be supplemented for fluorescence or absorption measurements, e.g., in the manner described in more detail with FIG. 2.

The arrangement of FIG. 1 is already directly suitable for luminescence measurements, but of course an about tenfold focal length of the lens array 21, 22, 23 is preferred for this, whereby the sensed sample volume is increased.

The arrangement of FIG. 2 is designed as a fluorescence reader. Firstly, it has the same elements as in FIG. 1, namely a microtiter plate 1 with wells 11$i$, minilens array 2$i$ with 96 lenses, large (41) and small (42) telescope lenses, with the field lens 5 therebetween and the CCD array 6. However, as a variant, the minilens array 2$i$ collimates, and there is no aperture grid pattern plate; however, directly in front of the CCD array there is a microlens array 7, with 96 microlenses which are collectively produced in microstructure technology and which effect the imaging into the detector cells of the CCD array 6.

A grid pattern dimension on the CCD array of about forty detector cells in diameter is thus attained, in which about one spot, twenty detector cells in diameter, of each sample element is illuminated.

A coupling-in mirror 8 (dichroic mirror) is arranged between the telescope lens 42 and the microlens array 7. An illuminating device 9 provides, via optical fibers 91 and condenser 92, illuminating light to the mirror 8, to be conducted by means of the already described optical system precisely to the places on the microtiter plate 1 which are imaged on the CCD detector 6. The light of the illuminating device 9 is thus optimally used for the measurement. Disturbances due to illumination of the structure of the microtiter plate 1 and the like are eliminated.

The illuminating device can consist of a white light source, e.g., a xenon gas discharge lamp, and may also be combined with a monochromator for the formation of a spectrophotometer.

A line source, e.g., a laser, can also be considered for use. With a discrete scanning device for the relative movement of the microtiter plate 1 and the minilens array 2$i$, including the whole optical arrangement, a 384-well microtiter plate, for example, can be completely read out with four successive positionings.

The usual filters in the illumination beam path and analyzing beam path, for the separation of illumination light and fluorescence light, can be arranged, together with the dichroic mirror, in an interchangeable module, so that a quick change of the fluorescence system is made possible.

For the same reason, preferably at least the lens array 2$i$ on the object side is achromatized, in that each individual lens is replaced by a lens group with achromatic correction. The spectral region is then typically provided as about 350–800 nm.

If the beam splitter 8 is not dichroically constituted and if a mirror is arranged over the microtiter plate 1, an arrangement can thus be derived for absorption measurement, analogous to the described equipment of the firm Molecular Dynamics. A reflected light illumination can of course also be provided.

The arrangement is confocal in the sense that a spatially bounded illumination spot in the sample is superposed with a spatially bounded detection region. The aperture in the illumination beam path can be represent by the fiber end or an illumination field stop; the aperture in the detection beam path can be produced by selective reading-out of the CCD pixels in the region of the individual illumination spots, by an aperture array in front of the CCD camera, or by a field stop in the region of the field lens.

A transmission illumination can also be realized with this confocal character, if a corresponding lens array like the lens array 2$i$ is provided.

In the embodiment as a reader for fluorescence measurements, a focus diameter of 50–500 $\mu$m, particularly 150 $\mu$m, with a numerical aperture of 0.6–0.7, is preferably provided.

Fluorescence correlation spectroscopy (FCS) can be parallelized with the same optical concept and can thus be useful for high throughput applications. However, for a good signal-to-noise ratio here, the reduction of the measurement volume to the range of femtoliters, with a focus diameter of 0.1–10 $\mu$m, is advantageous. The minimum correlation time is however limited by the integrating and readout time of the CCD array. Detector arrays which can be read out in parallel, such as APD arrays, are therefore to be preferred in this application.

For easy adaptation to the different measurement processes, a reader having a modular construction is therefore proposed, in which the lens array 2$i$ on the sample side is interchangeable.

The following advantages of the invention can thus be derived:

High channel number with an order of magnitude of $10^2$ channels is easily possible and gives effective parallelization.

A high fluorescence detection sensitivity is provided by the large possible aperture of the individual cells 21, 22, 23 of the minilens array.

A low power of the light source 9 is sufficient, since the illumination takes place in a structured manner, and a high fluorescence detection sensitivity is provided.

A strong suppression, by the confocal detection, of interfering fluorescence from outside the measurement volume (typical measurement volumes in fluorescence measurements for microtiter plates and 96-channel optics: a few nanoiliters) makes possible the measurement of homogeneous samples, in spite of possible strong fluorescence concentrations on the floor due to precipitates and in spite of strong inherent fluorescence of the floors and walls of the wells in the microtiter plate.

An independence from filling height in fluorescence measurements is likewise effected by the confocal character.

Fluorescence filters and beam splitters with standard dimensions (diameter in the region of 25 mm) can be used, since the greatest dimensions of the microtiter plates are reduced by the telescope (diameter about 15 mm at the CCD array).

Crosstalk between adjacent samples (wells) is in principle small due to the local illumination and the confocal detection, and can be further reduced by an aperture mask or by lands between the lens elements of the lens array, and the simultaneous use of, for example, only every other well (e.g., 96-channel detection with 384-microtiter plates).

Data sensing is also simple with the high channel number due to the use of a CCD array.

Flexibility in the format is provided, since the 96 grid pattern of the reader also matches more highly integrated microtiter plates (e.g., 384, 864, 1536 wells) and also so-called cell chips and DNA chips.

Kinetic fluorescence measurements are in particular supported by the multi-channel embodiment.

Fluorescence measurements can be carried out on cell-based arrays by focusing the lens array 2i on cells which are installed on the floor of the well. Positionally resolved reading-out of the individual spot, here as large as possible, on the CCD with a resolution of about the cell size or better makes possible a substantially more detailed, positionally resolved, analysis of the biological function of the substance to be investigated. This High Content Screening (HCS) makes possible, e.g., the comparison of the fluorescence concentrations outside, on, and within the cell, and in the cell nucleus. Here also, kinetics is important.

What is claimed is:

1. A reader for microtiterplates or substance chips having a plurality of individual sample volumes arranged in a grid pattern dimension, comprising:
    a lens array having a grid pattern dimension that corresponds to said grid pattern dimension of said individual sample volumes of a microtiterplate or substance chip,
    a detector array,
    a reflected light illumination device providing illumination light,
    a telescope between said lens array and said detector array that effects a reduction to match a beam diameter defined by said lens array to the dimensions of said detector array, and
    a field lens,
    wherein a reduced image of said microtiterplate or substance chip is formed on said detector array by a system of said lens array, said telescope, and said field lens, so that on said detector array a strict channel separation results between measurement signals arising from said individual sample volumes of said microtiterplate or substance chip,
    wherein said lens array is achromatized in that each individual lens of said lens array comprises a lens group with achromatic properties, and
    wherein said illumination light is conducted through said lens array precisely to locations on said microtiterplate or substance chip which are imaged on said detector array.

2. The reader according to claim 1, wherein said telescope comprises a respective lens arranged between said lens array and said field lens, and between said field lens and said detector array.

3. The reader according to claim 2, wherein said lens array comprises individual lenses that are arranged with respect to each other in a formal 8*12.

4. The reader according to claim 1, further comprising a microlens array arranged in front of said detector array in the direction of said microtiter plate or substance chip.

5. The reader according to claim 1, further comprising a reflected-light illumination device integrated with said system.

6. The reader according to claim 1, further comprising an aperture array arranged between said lens array and said field lens.

7. The reader according to claim 6, further comprising a dichroic mirror for coupling-in said illumination device.

8. The reader according to claim 1, wherein said detector array comprises a CCD array or a photodiode array.

9. The reader according to claim 1, having a modular construction with an interchangeable lens array.

10. A reader for microtiterplates or substance chips having a plurality of individual sample volumes arranged in a grid pattern dimension, comprising:
    a lens array having a grid pattern dimension that corresponds to said grid pattern dimension of said individual sample volumes of a microtiterplate or substance chip,
    a detector array,
    a reflected light illumination device providing illumination light,
    a telescope between said lens array and said detector array that effects a reduction to match a beam diameter defined by said lens array to the dimensions of said detector array, and
    a field lens,
    wherein a reduced image of said microtiterplate or substance chip is formed on said detector array by a system of said lens array, said telescope, and said field lens, so that on said detector array a strict channel separation results between measurement signals arising from said individual sample volumes of said microtiterplate or substance chip,
    said reader comprising a modular construction with said lens array being interchangeable, and
    wherein several lens arrays are provided, and
    wherein the individual lenses of different ones of said several lens arrays provide different numerical apertures.

11. The reader according to claim 10, wherein said telescope comprises a respective lens arranged between said lens array and said field lens, and between said field lens and said detector array.

12. The reader according to claim 11, wherein said lens array comprises individual lenses that are arranged with respect to each other in a formal 8*12.

13. The reader according to claim 10, further comprising a microlens array arranged in front of said detector array in the direction of said microtiter plate or substance chip.

14. The reader according to claim 10, further comprising a reflected-light illumination device integrated with said system.

15. The reader according to claim 10, further comprising an aperture array arranged between said lens array and said field lens.

16. The reader according to claim 15, further comprising a dichroic mirror for coupling-in said illumination device.

17. The reader according to claim 10, wherein said lens array is achromatize in that each individual lens comprises a lens group with achromatic properties.

18. The reader according to claim 10, wherein said detector array comprises a CCD array or a photodiode array.

19. A reader for microtiterplates or substance chips having a plurality of individual sample volumes arranged in a grid pattern dimension, comprising:
- a lens array having a grid pattern dimension that corresponds to said grid pattern dimension of said individual sample volumes of a microtiterplate or substance chip,
- a detector array,
- a reflected light illumination device providing illumination light,
- a telescope between said lens array and said detector array that effects a reduction to match a beam diameter defined by said lens array to the dimensions of said detector array, and
- a field lens,
- wherein a reduced image of said microtiterplate or substance chip is formed on said detector array by a system of said lens array, sad telescope, and said field lens, so that on said detector array a strict channel separation results between measurement signals arising from said individual sample volumes of said microtiterplates or substance chip,
- said reader comprising a modular construction with said lens array being interchangeable,
- wherein several lens arrays are provided,
- wherein the individual lenses of different ones of said several lens arrays provide different numerical apertures,
- wherein said lens array is achromatized in that each individual lens of said lens array comprises a lens group with achromatic properties, and
- wherein said illumination light is conducted through said lens array precisely to locations on said microtiterplate or substance chip which are imaged on said detector array.

* * * * *